United States Patent [19]

Scott

[11] Patent Number: 4,683,042
[45] Date of Patent: Jul. 28, 1987

[54] METHOD AND APPARATUS FOR CONTINUOUS ANNULAR ELECTROCHROMATOGRAPHY

[75] Inventor: Charles D. Scott, Oak Ridge, Tenn.

[73] Assignee: The United States of America as represented by the United States Department of Energy, Washington, D.C.

[21] Appl. No.: 857,228

[22] Filed: Apr. 29, 1986

[51] Int. Cl.⁴ ..................... G01N 27/26; G01N 27/28
[52] U.S. Cl. ................. 204/180.1; 204/272; 204/299 R
[58] Field of Search ............... 204/299 R, 180.1, 272

[56] References Cited

U.S. PATENT DOCUMENTS

| | | | |
|---|---|---|---|
| 3,085,956 | 4/1963 | Caplan | 204/299 R |
| 3,197,393 | 7/1965 | McEven | 204/299 R |
| 3,556,967 | 1/1971 | Anderson | 204/299 R |
| 3,616,453 | 10/1971 | Leger | 204/299 |
| 3,640,813 | 2/1972 | Nerenberg | 204/299 R |
| 3,704,217 | 11/1972 | Nerenberg | 204/299 R |
| 3,844,926 | 10/1974 | Smyth et al. | 204/299 |
| 4,040,940 | 8/1977 | Bier | 204/299 R |
| 4,149,957 | 4/1979 | Gibson et al. | 204/299 R |
| 4,182,678 | 1/1980 | Ito | 210/198 C |
| 4,315,812 | 2/1982 | Karlson | 204/299 R |
| 4,432,849 | 2/1984 | Saito | 204/299 R |

FOREIGN PATENT DOCUMENTS 2152952  8/1985  United Kingdom ............ 204/299 R

OTHER PUBLICATIONS

McDonald et al., "Centrifugal Force in Paper Chromatography and Electrophoresis," Analytical Chemistry, vol. 31, No. 5, May 1959, pp. 825-829.
Vermuelen et al., "Design Theory and Separations in Preparative-Scale Continuous-Flow Annular-Bed . . . ", Eng. Chem., 1971.
"Continuous Annular Chromatography—Contributions to the Literature", (1976-1984).
"R&D Accomplishments at ORNL", distributed Sep. 3, 1975, Summer 1975.

Primary Examiner—John F. Niebling
Assistant Examiner—Terryence Chapman
Attorney, Agent, or Firm—Stephen D. Hamel; Judson R. Hightower

[57] ABSTRACT

Separation of complex mixtures and solutions can be carried out using a method and apparatus for continuous annular electrochromatography. Solutes are diverted radially by an imposed electrical field as they move downward in a rotating chromatographic column.

16 Claims, 4 Drawing Figures

METHOD AND APPARATUS FOR CONTINUOUS ANNULAR ELECTROCHROMATOGRAPHY

The United States government has rights to the present invention pursuant to a contract between the U.S. Department of Energy and Martin Marietta Energy Systems, Inc.

BACKGROUND OF THE INVENTION

The present invention relates to a system for the continuous separation of mixtures of complex solutes in aqueous solution by the simultaneous use of annular chromatography and electrophoresis.

The separation of complex aqueous mixtures of solutes is especially difficult to accomplish on a continuous basis. The separation of mixtures of macromolecules such as proteins and synthetic polymers is particularly difficult. In the past, such complex mixtures have been separated, for example, by continuous electrophoresis, which combines effects of fluid flow and electrolyte migration at right angles to an imposed electrical field. See Vermeulen et al, "Design Theory and Separation in Preparative-scale Continuous-flow Annular-bed Electrophoresis," *Ind. Eng. Chem. Process Des. Develop.* 10(1): 91–101 (1971). According to Vermeulen et al, uniform flow through an electrochromatographic column is achieved by the use of a bed-packing which is comprised of like-sized, spherical particles, that act as an "anticonvectant."

U.S. Pat. No. 3,616,453 discloses a continuous electrophoretic separation device that includes an annular chamber, extending between an outer and an inner cylindrical wall, through which a continuous flow of dilute electrolyte is directed axially. A radial potential gradient is established in the dilute electrolyte, so that components of a complex mixture introduced into the annular chamber migrate radially at differing rates, thereby separating liquid flowing through the chamber into differing radial laminae. At least the outer cylindrical wall is continuously rotated to provide a centrifugal field across the annular chamber which inhibits mixing of these laminae. The inner wall can also be rotated to give an annular separation chamber which is "angular velocity gradient"-stabilized.

U.S. Pat. No. 3,844,926 discloses improved inlet means by which the dilute electrolyte eluant and the mixture to be separated can be introduced into the annular chamber of the above-described separation device. The disclosed improvement does not overcome, however, certain drawbacks to the basic separation device taught by U.S. Pat. No. 3,616,453. First, the disclosed separation system employs a fast-moving rotor to provide the rapid rotation of the cylindrical wall that is necessary to achieve desired fluid dynamic stability in the annular chamber. The requirement for a rapidly moving rotor substantially complicates system design. Second, separation via the disclosed system is essentially one-dimensional, i.e., components of a mixture introduced into the annular chamber can be separated only radially.

Another approach to multicomponent separation on an industrial scale utilizes continuous annular chromatography (CAC). The operation of a continuous, annular chromatograph involves moving an annular bed of sorbent past a stationary feed entry point and stationary effluent recovery ports. As the annulus rotates, material to be separated is introduced, over a short feed-introduction time, followed by a relatively longer period of elution from a series of eluent nozzles. During this operational sequence, the initial entry point completes a revolution. As elution proceeds, the eluted substances progress down the annulus, giving the appearance of helices as the annulus rotates. The more strongly sorbed species exit from the rotating annulus at a greater distance from the feed point, thus providing a continuous "circumferential" separation of species with differing sorption characteristics. See, generally, Scott et al, "Pressurized, Annular Chromatograph for Continuous Separations," *J. Chromatogr.* 126: 381–400 (1976), the contents of which are hereby incorporated herein by reference. In this fashion, hafnium and zirconium, a system of importance to the nuclear fuel cycle, have been separated. Begovich et al, "Continuous Ion Exchange Separation of Zirconium and Hafnium Using an Annular Chromatograph," *Hydrometallurgy* 10: 11–20 (1983). Nevertheless, CAC provides, like continuous electrophoresis, only one-dimensional separation capability.

SUMMARY OF THE INVENTION

It is therefore an object of the present invention to provide a method for separating complex aqueous mixtures in a manner that is both continuous and truly two-dimensional, i.e., components of a mixture can be separated both radially and circumferentially at the same time.

It is also an object of the present invention to provide apparatus for high-resolution, continuous separation of complex aqueous mixtures, including biochemical mixtures, without the need for high-speed rotors.

In accomplishing the foregoing objects, there has been provided, in accordance with one aspect of the present invention, a method for separation of solutes in an aqueous sample, comprising the steps of (1) imposing an electrical potential gradient radially through a rotatable annulus comprised of an adsorbent, the annulus having a first and a second end; then (2) introducing, at a predetermined point at the first end of the annulus, a fluid sample comprising at least one separable constituent while continuously rotating the annulus, such that the predetermined point is stationary relative to the rotating annulus; and (3) thereafter eluting the sample from the second end of the annulus, whereby the constituent is separated radially and circumferentially.

In accordance with another aspect of the present invention, apparatus has been provided for effecting the above-described separation method. The apparatus comprises a rotatable annulus, comprised of an adsorbent material, having a first and a second end; means for rotating the annulus; means for imposing an electrical potential gradient radially through the annulus; means for introducing a feed stream at a predetermined point at the first end of the annulus, the predetermined point being stationary relative to rotation of the annulus; and means for collecting a desired fraction from the second end of the annulus.

Other objects, features, and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENT

In the present invention, a conventional continuous annular chromatograph is modified, in accordance with the present invention, to incorporate electrodes (see FIG. 1) that permit the imposition of a radial electrical field on the rotating annulus of the chromatograph. Solutes of a complex mixture or solution are introduced into the top of the annulus from a feed point which is stationary relative to the slowly rotating annulus. The solutes are diverted in a radial direction by the imposed field as they move through the annulus. Consequently, the separated solutes migrate down the annulus as helical bands, radial symmetry being maintained without the use of high-speed rotors. Thus, no centrifugal field is employed to stabilize the solute bands; rather, the solid adsorbent provides fluid dynamic stability in the annulus while enhancing separation. Moreover, the action of the electrical field provides a second dimension of separation (radial, in addition to circumferential) that gives a higher resolution for the separation system of the present invention than is possible with either continuous electrophoresis or CAC.

Figure 1:
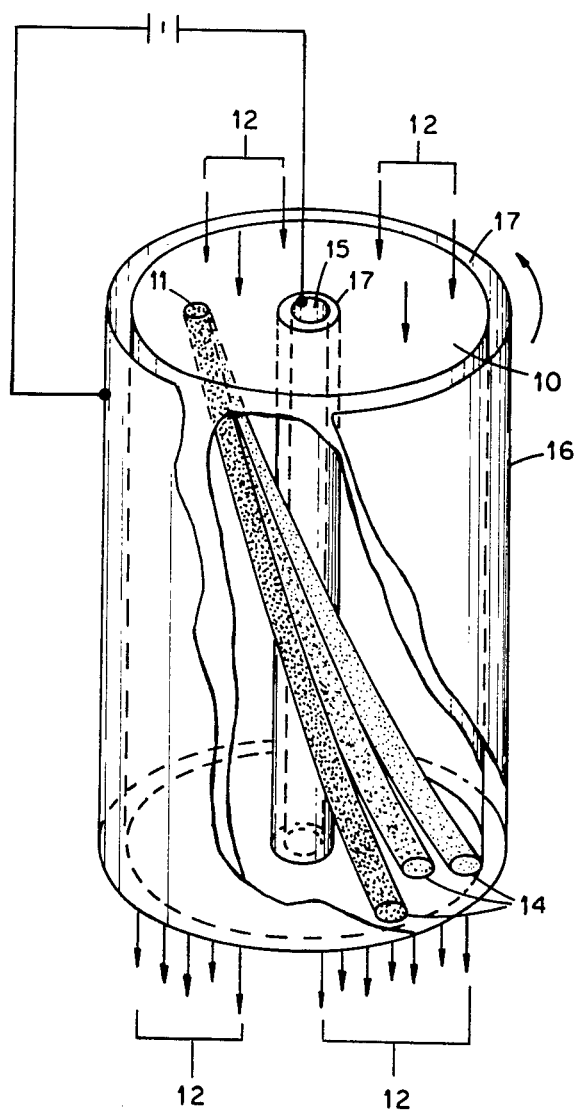
FIG. 1 is a schematic drawing of electrochromatographic apparatus within the present invention.

With reference to FIG. 1, the electrochromatographic apparatus of the present invention comprises a rotatably mounted cylinder with an annulus 10 of adsorbent material (sorption bed). A suitable mechanism (not shown) is provided for rotating the cylinder at a speed permitting elution of a given sample within a predetermined period, which preferably is no greater than one annular revolution. More specifically, for a mixture or solution comprising two or more separable constituents, it is preferable that the slowest-migrating constituent be eluted from the column within one rotation after the fastest-migrating constituent is eluted. Although more than one annular revolution can separate elutions of the fastest- and slowest-migrating constituents, respectively, undesirable mixing of the corresponding constituent bands in the column would likely occur.

The feed stream 11, comprising a mixture or solution to be separated, is introduced at a fixed opening at the top of the cylinder. Eluent 12 is added at the top of the cylinder across the entire cross section of the annulus. If gradient elution is desired, then multiple nozzles for eluent introduction can be used, with the eluent level maintained below the top of the head space to allow sufficient room for the removal of potentially explosive electrode gases and to provide system overpressure.

The eluate is discharged through a series of discharge tubes 13 arranged in a predetermined pattern, preferably concentric, at the bottom of the cylinder. The separated solutes can be collected continuously at discrete exit ports 14, preferably arranged in radial rows, around the bottom of the absorbent annulus. Each exit port can include a small porous filter at its entrance and terminate with a small drip tube. Products are collected by placing a stationary collection channel at the angular and radial position determined for product elution, as described in detail below.

The electrical field is imposed by a power source through electrodes 15 and 16, respectively, that can be immediately adjacent to the outer and inner walls of the absorbent annulus. Alternatively, the electrodes can be separated from the adsorbent by porous membranes. If high current flow is expected, then cooling of the electrodes and the adsorbent bed material is preferably effected by annular channels 17 between the respective electrodes and the adsorbent bed, or by cooling external to the active adsorbent annulus around the outside of the outer electrode and internal to the inner electrode. The electrodes are preferably constructed of a material that is compatible with (i.e., substantially nonreactive in) electrically-driven oxidative and reductive processes. For example, inner electrode 15 can be fabricated from solid graphite or a sheet, a perforated plate, or wire mesh comprised of a noble metal, such as gold-plated nickel. The outer electrode 16 can be nickel or a more stable nickel-based alloy sheet, perforated plate, or wire mesh.

When high flow-rates are used, pressurized operation of the electrochromatograph of the present invention is required. Constant pressure can be maintained by gas overpressure in the head space at the top enclosure of the system. All entrance and exit streams and electrode connectors at the top of the column progress through a central stationary shaft with a pressure seal, thus allowing rotation of the annulus under pressurized operation.

A gas sweep stream can be used to reduce the hazard of electrolysis gas. When a coolant is circulated through annular channels 17, for example, the liquid coolant stream can also be used to sweep out any electrode gases ($H_2$ or $O_2$) which are generated. In the embodiment of the present invention wherein the electrodes are separated from the adsorbent by porous membranes, the resulting electrode annuli separate any resulting off-gas from the adsorption bed, and a small electrode buffer stream can be used to sweep out the off-gas and to provide column cooling.

As previously indicated, the present invention provides for a two-dimensional separation, i.e., each separated product exits from the annular electrochromatography system of the present invention at a position reflecting radial and angular components which depend on the geometry and dynamics of the system and on the sorption and electrophoretic properties of the solutes. In general, the chromatographic aspect of the separation process contributes to the angular component of product position, while the electrophoretic aspect affects the radial component.

To determine the position for product elution from an annular electrochromatograph of the present invention, reference is made to the demonstration by Scott et al, cited above, that angular displacement ($\bar{\theta}$) in the absence of an electric field can be represented by the equation:

$$\bar{\theta} = (L\omega/u_f)[\epsilon + (1-\epsilon)\kappa] \qquad (1)$$

where,
$\bar{\theta}$ = angular displacement in radians (rads) of the maximum solute concentration exiting the annulus,
L = vertical distance (cm) from feed point to exit, $\omega$ = rotational speed (rad/s) of the column,
$u_f$ = superficial eluent velocity (cm/s) through the column,
$\epsilon$ = void fraction (cm³ fluid phase/cm³ total volume) in the chromatographic column, and
$\kappa$ = distribution coefficient, expressed as, $$\frac{\text{moles solute/cm}^3 \text{ sorbent phase}}{\text{moles solute/cm}^3 \text{ fluid phase}}$$

The extent of angular displacement $\theta$ reflects sorption phenomena within the adsorbent annulus, as well as the geometry and dynamics of the column.

Figure 2:
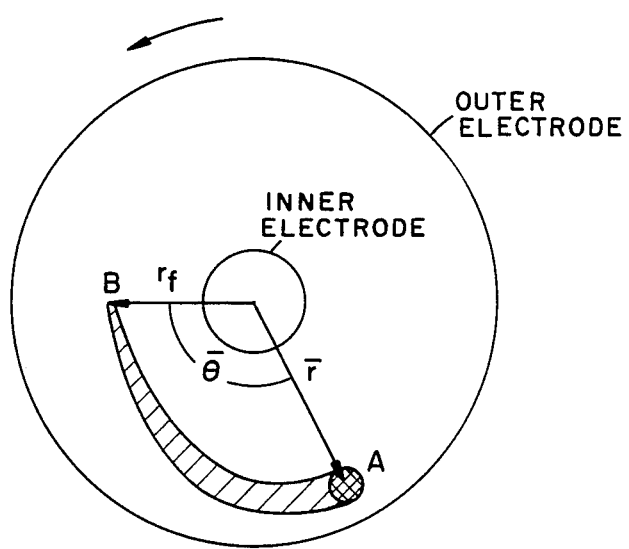
FIG. 2 is a schematic drawing that provides a top view of an electrochromatograph effected in accordance with the present invention.

Imposition of an electric field in accordance with the present invention results in a radial deflection of a solute which is dependent on the electrophoretic mobility of the solute in the nonsorbed state. There will be only limited radial mobility during the time the solute is sorbed in or on the stationary phase; but, since this will also be true for migration in the vertical direction, these effects cancel out and migration rates can be considered in the whole adsorption bed. If constant electrophoretic properties are assumed throughout the column, the apparent radial distance of solute movement (see FIG. 2) can be expressed as:

$$\bar{r} = r_f = L \tan \alpha \tag{2}$$

where
$\bar{r}$ = radial position (cm) of the exit of the maximum solute concentration A,
$r_f$ = radial position (cm) of the feed point B,
$L$ = column length (cm), and
$\alpha$ = angle (rads) of radial deflection of the solute.

The angular deflection is also dependent on the relative axial and radial movements:

$$\tan \alpha = v_e/v_a \tag{3}$$

where,
$v_e$ = electrophoretic mobility (cm/s) in the adsorbent bed, and
$v_a$ = axial velocity (cm/s) of the solute through the adsorbent bed.

The axial velocity of a solute through the column can be described as the length of the column divided by the length of time for the solute to pass through the column, and can be expressed as:

$$v_a = L\omega/\bar{\theta} \tag{4}$$

In practice, $v_e$ for a given solute can be determined empirically in a stationary analytic electrophoresis system. The system produced by Bio-Rad, Inc. (Richmond CA) is illustrative of the various standard analytic electrophoresis systems that are commercially available. By the same token, $v_a$ can be determined empirically in a standard stationary analytic chromatography system. One such suitable system is manufactured by Hewlett Packard Corp. (Avondale PA).

By combining the above-described relationships, the radial discharge point for a given solute is calculated as:

$$\bar{r} = r_f + (v_e \bar{\theta}/\omega) \tag{5}$$

or $$\bar{r} = r_f + (v_e L/u_f)[\epsilon + (1-\epsilon)] \tag{6}$$

Thus, each solute exits the column at a specific position, reflecting both $\theta$ and $\bar{r}$, which is totally dependent on the adsorption and electrophoretic properties of the solute. Angular displacement $\theta$, which represents the rate at which a solute moves through the adsorbent annulus, is determined in part by rotational speed $\omega$.

When two or more constituents of a mixture or solution are to be separated in accordance with the present invention, at least a corresponding number of exit ports are provided at positions determined pursuant to the above-described relationships. If more exit ports than the number of solutes to be separated are provided, then the chromatographic apparatus of the present invention can also include gating means for controlling access from the column to those ports that are to receive solute. For example, a microprocessor programmed to activate values at each such port can be used for this purpose.

EXAMPLES

Separation of Bovine Hemoglobin and/or a starch gum colloid

Figure 3:
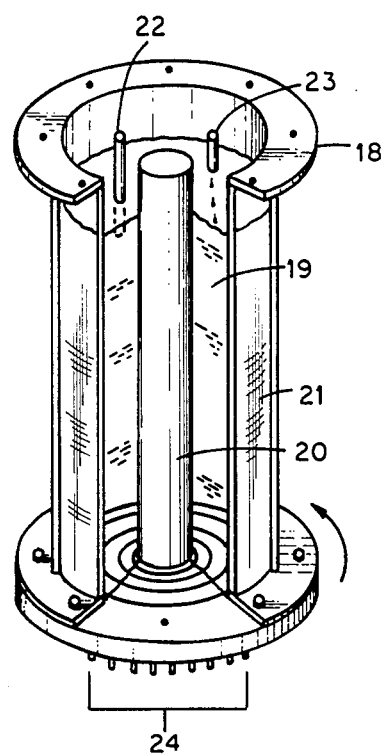
FIG. 3 is a drawing that provides a partial cross-sectional perspective view of a device used to carry out the separation method of the present invention.

The separation method of the present invention was carried out in a system shown schematically in FIG. 3. An adsorbent column 18 was set up, comprising a sorption medium 19, such as glass beads or polyacrylamide resin (e.g., BIOGEL P-150 ®, manufactured by Biorad, Inc., Richmond CA) and having a 30-cm active height, an inner diameter of 8.8-cm and an annulus of approximately 3.8-cm. The column was externally jacketed by an ice bath for cooling, and was equipped with an inner graphite electrode 20 (approximately 1.25 cm diameter) and an outer nickel-mesh electrode 21. The column was slowly rotated, and provision was made for the introduction of a continuous feed stream and an eluent stream at stationary nozzles 22 and 23, respectively, at the top of the column. (Nozzle 22 was positioned about 0.5 cm below, and nozzle 23 just above, the surface of the sorption bed to prevent mixing of the feed and eluent.) The electrodes were connected to an external DC power supply (not shown) and the eluate was withdrawn through a concentric series of filtered nozzles 24.

Bovine hemoglobin and/or a starch gum colloid (e.g., Blue Dextrin 2000 ®) were introduced in the feed stream, at a rate of between 1% and 5% of the eluent rate, to the system shown in FIG. 3. In all tests, a phosphate buffer (nominal pH of about 8.0) was used. Measurement of solute concentration was accomplished spectrophotometrically at 410 nm (hemoglobin) and 610 nm (starch gum).

When the polyacrylamide resin BIOGEL P-150 ® (molecular exclusion limit of 150,000 daltons) was used, but no electrical potential gradient established between the inner and outer electrodes, hemoglobin and the starch gum could be eluted in only a relatively narrow band. In accordance with the present invention, however, the components of hemoglobin—there are at least five different molecular species—could be made to migrate towards the outer electrode when an electrical current was imposed (see Table 1). The degree of migration was dependent on the residence time within the column and the strength of the electrical field. Thus, residence time was low when noninteracting glass beads were used, but when the polyacrylamide resin was used as a molecular sieve, the hemoglobin did interact with, and progressed more slowly through, the column.

TABLE 1
ELUTION OF HEMOGLOBIN IN AN 8.8-cm-diam ELECTROCHROMATOGRAPH

| ω (rad/s × $10^4$) | $\bar{\theta}$ (rad) | ΔE (V) | \multicolumn{6}{c}{FRACTION OF HEMOGLOBIN ELUTED AT RADIAL POSITIONS (cm)} |
|---|---|---|---|---|---|---|---|---|
| | | | (−) | 1.7 | 2.5 | 3.3 | 4.0 | (+) |
| \multicolumn{9}{c}{GLASS BEADS (RESIDENCE TIME ~18 min)} |
| 0 | 0 | 0 | | 0.01 | 0.01 | 0.97 | 0.01 | |
| 0 | 0 | 5 | | 0.03 | 0.10 | 0.86 | 0.01 | |
| 0 | 0 | 20 | | 0.16 | 0.31 | 0.51 | 0.02 | |
| \multicolumn{9}{c}{BIOGEL P-150 ® (RESIDENCE TIME ~100 min)} |
| 0 | 0 | 0 | | 0.02 | 0.08 | 0.77 | 0.14 | |
| 0 | 0 | 010 | | 0.38 | 0.26 | 0.27 | 0.08 | |
| 0.41 | 105 | 10 | 0.43 | 0.17 | 0.29 | 0.10 | | |

A continuous and combined chromatographic/electrophoretic separation was effected, in accordance with the present invention, when the starch gum and hemoglobin were simultaneously eluted through the column while the column was slowly rotated. An external ice bath was used to remove electrically generated heat. Nevertheless, only a modest electrical potential could be used without excessive bed temperatures when the eluent flow was less than 10 ml/min. (The bed temperature was not allowed to exceed 35° C.)

Figure 4:
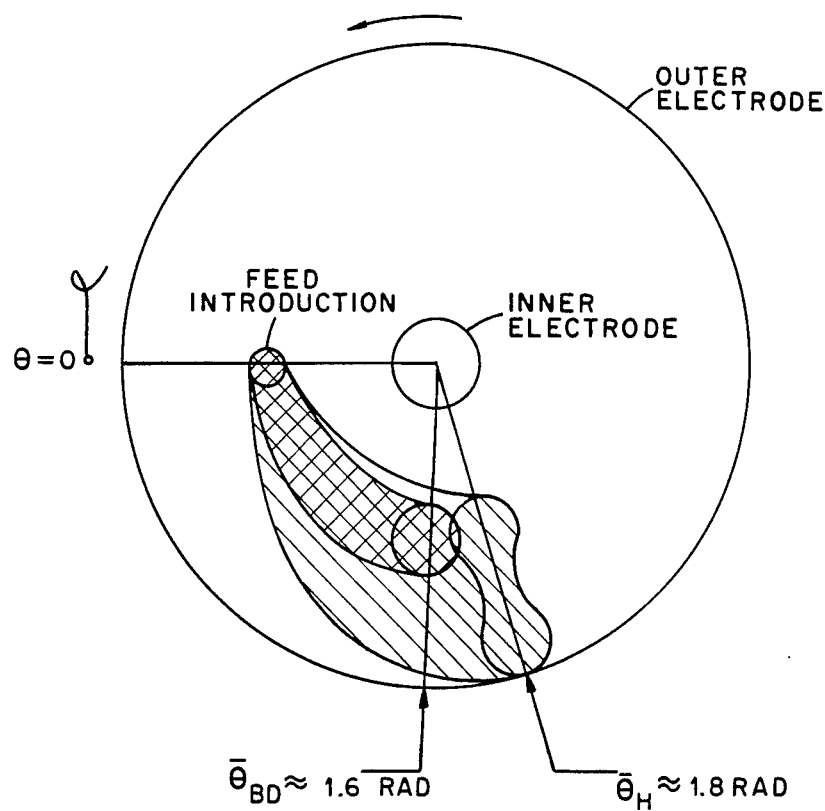
FIG. 4 is a schematic illustration of the electrochromatograph separation pattern of starch gum and hemoglobin which was generated using the present invention.

The starch gum, which has a very large molecular weight and will not interact with the polyacrylamide resin, was eluted first (angular displacement $\bar{\theta}$BD of about 1.6 rads) to separate it from the hemoglobin fractions by chromatographic action, as shown in FIG. 4. The hemoglobin was eluted later (angular displacement $\bar{\theta}_H$ of about 1.8 rads), and radial separations of at least two fractions due to differences in electrophoretic mobility were observed, even at a potential of 10 V. Simultaneous electrophoresis and chromatography (electrochromatography) was thereby demonstrated.

The present invention permits the simultaneous use of chromatographic and electrophoretic separation processes in a single step and on a continuous basis. Although there are continuous annular chromatographic systems, and attempts have been made to achieve continuous electrophoresis, a combination of these two powerful separation forces on a continuous basis has not been achieved before. The separation system of the present invention will be particularly useful in the preparative-scale separation of macromolecules, for example, in biotechnology and the biomedical sciences.

What is claimed is:

1. A method for separation of solutes in an aqueous sample, comprising the steps of:
   (a) imposing an electrical potential gradient radially through a rotatable annulus comprised of an adsorbent material, said annulus having a first and a second end; then
   (b) introducing, at a predetermined point at said first end of said annulus, a fluid sample comprising at least one separable constituent while continuously rotating said annulus, such that said predetermined point is stationary relative to the rotating annulus; and thereafter
   (c) eluting said sample from said second end of said annulus such that said constituent is collected at said second end at a radial position $\bar{r}$ which is determined as a function of $r_f$, $\bar{\theta}$, $V_e$ and ω, where
   $\theta$ = angular displacement of said constituent in said annulus;
   $r_f$ = distance of said predetermined point from the center of said annulus;
   $V_e$ = electrophoretic mobility of said constituent in said adsorbent material; and
   ω = rotational speed of said annulus.

2. A method as claimed in claim 1, wherein step (c) comprises eluting said constituent from said annulus within a single revolution of said annulus.

3. A method as claimed in claim 1, where the radial position $\bar{r}$ conforms to the relationship $\bar{r} = r_f + (V_e\bar{\theta}/\omega)$.

4. A method as claimed in claim 1, wherein said adsorbent comprises a molecular sieve.

5. A method as claimed in claim 4, wherein said molecular sieve is a polyacrylamide resin.

6. A method as claimed in claim 1, wherein said adsorbent comprises glass beads.

7. A method as claimed in claim 1, further comprising the step of sweeping from said annulus gases generated by imposition of said electrical potential.

8. A method as claimed in claim 1, wherein said aqueous sample comprises at least two separable constituents and step (c) comprises withdrawing fluid from said annulus through a plurality of filtered exit ports.

9. Apparatus for annular electrochromatography, comprising:
   (a) a rotatable annulus comprised of an adsorbent material, said annulus having a first and a second end;
   (b) means for rotating said annulus;
   (c) means for imposing an electrical potential gradient radially through said annulus;
   (d) means for introducing, at a predetermined point at said first end of said annulus, a feed stream comprising at least one separable constituent, said predetermined point being stationary relative to rotation of said annulus; and
   (e) means for collecting a desired fraction from said second end of said annulus at a radial position which is determined as a function of $r_f$, $\theta$ and ω, where
   $\theta$ = angular displacement of said constituent in said annulus;
   $r_f$ = distance of said predetermined point from the center of said annulus;
   $V_e$ = electrophoretic mobility of said constituent in said adsorbent material; and
   ω = rotational speed of said annulus.

10. Apparatus as claimed in claim 9, wherein said function is $r = r_f + (v_e\bar{\theta}/\omega)$.

11. Apparatus as claimed in claim 9, wherein means (e) comprises a plurality of exit ports, each provided at said second end of said annulus at a position which is determined, respectively, in accordance with said function.

12. Apparatus as claimed in claim 9, wherein means (e) comprises a plurality of exit ports, each provided at said second end of said annulus, and gating means for accessing said exit ports in a predetermined pattern which is a function of $r_f, \bar{\theta}, V_e$ and ω.

13. Apparatus as claimed in claim 9, wherein means (c) comprises a first electrode and a second electrode between which said electrical potential gradient is imposed.

14. Apparatus as claimed in claim 13, further comprising means for bringing at least one of said first and second electrodes into contact with a coolant.

15. Apparatus as claimed in claim 13, wherein said first and second electrodes are each separated from said annulus by a porous membrane.

16. Apparatus as claimed in claim 9, further comprising means for pressurizing said annulus.

* * * * *